United States Patent
Tzeng et al.

(10) Patent No.: US 6,492,373 B2
(45) Date of Patent: Dec. 10, 2002

(54) 6-FLUORO-1,4-DIHYDRO-7-[4-(2-HYDROXYIMINOETHYL)-1-PIPERAZINYL]-4-OXOQUINOLINE-3-CARBOXYLIC ACID DERIVATIVES, THEIR PREPARATION AND PHARMACEUTICAL COMPOSITIONS

(75) Inventors: Cherng-Chyi Tzeng, Kaohsiung (TW); Yeh-Long Chen, Kaohsiung (TW); Feng-Nien Ko, Taipei (TW)

(73) Assignee: Pharmaceutical Industry Technology and Development Center (TW)

( * ) Notice: Subject to any disclaimer, the term of this patent is extended or adjusted under 35 U.S.C. 154(b) by 0 days.

(21) Appl. No.: 10/002,733

(22) Filed: Nov. 15, 2001

(65) Prior Publication Data

US 2002/0061895 A1 May 23, 2002

Related U.S. Application Data

(62) Division of application No. 09/489,058, filed on Jan. 21, 2000, now abandoned.

(30) Foreign Application Priority Data

Jan. 12, 2000 (TW) ........................................ 89100389 A

(51) Int. Cl.[7] ............................................. A61K 31/496
(52) U.S. Cl. .................. 514/253.08; 544/363
(58) Field of Search ....................... 544/363; 514/253.08

(56) References Cited

U.S. PATENT DOCUMENTS

| | | | | |
|---|---|---|---|---|
| 4,292,317 A | | 9/1981 | Pesson ........................ | 424/250 |
| 4,528,287 A | | 7/1985 | Itoh et al. .................... | 514/254 |
| 4,547,503 A | * | 10/1985 | Petersen et al. | |

FOREIGN PATENT DOCUMENTS

| | | | | |
|---|---|---|---|---|
| JP | 58069880 | | 4/1983 | ......... C07D/405/12 |
| JP | 63083083 | | 4/1988 | ......... C07D/405/12 |

OTHER PUBLICATIONS

Foroumadi et al., Chemical Abstracts, vol. 128, No. 164860 (1998).*
Chu et al., "Synthesis and Biological Activity of Benzothiazole[3,2-a]quinolone Antibacterial Agents", J. Med. Chem. 29:1531–1534, 1986.
Domagala et al., "1–Substituted 7–[3–[(Ethylamino)methyl]–1–pyrrolidinyl]–6,8–difluoro–1, 4–dihydro–4–oxo–3–quinolinecarboxylic Acids. New Quantitative Structure–Activity Relationships at $N_1$ for the Quinolone Antibacterials", J. Med. Chem. 31:991–1001, 1988.
Hayakawa et al., "Synthesis and Antibacterial Activities of Substituted 7–Oxo–2.3–dihydro–7H–pyrido[1,2,3–de][1,4] benzoxazine–6–carboxylic Acids", Chem. Pharm. Bull. 32:4907–4913, 1984.

Koga et al., "Structure–Activity Relationships of Antibacterial 6,7– and 7,8–Disubstituted 1–Alkyl–1, 4–dihydro–4–oxoquinoline–3–carboxylic Acids", J. Med. Chem. 23:1358–1363, 1980.

Kondo et al., "Studies on Prodrgus. 5.[1] Synthesis and Antimicrobial Activity of N–(Oxoalkyl)norfloxacin Derivatives", J. Med. Chem. 29:2020–2024, 1986.

Kondo et al., "Studies on Prodrugs. 11. Synthesis and Antimicrobial Activity of N–[(4–Methyl–5–methylene–2–oxo–1, 3–dioxolan–4–yl)oxy]norfloxacin", J. Med. Chem. 32:671–674, 1989.

Matsumoto et al., "Pyridonecarboxylic Acids as Antibacterial Agents. 2.[1] Synthesis and Structure–Activity Relationships of 1,6,7–Trisubstituted 1,4–Dihydro–4–oxo–1, 8–naphthyridine–3–carboxylic Acids, Including Enoxacin, a New Antibacterial Agent[2]", J. Med. Chem. 27:292–301, 1984.

* cited by examiner

*Primary Examiner*—Emily Bernhardt
(74) *Attorney, Agent, or Firm*—Fish & Richardson P.C.

(57) ABSTRACT

The present invention discloses a novel 6-fluoro-1,4-dihydro-7-[4-(2-hydroxyiminoethyl)-1-piperazinyl]-4-oxoquinoline-3-carboxylic acid derivatives (formula I), with a process for their preparation, and with pharmaceutical compositions containing them as the active ingredient for the treatment of bacterial infections and/or renal cancer diseases.

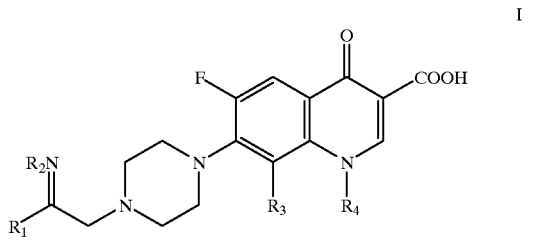

1 Claim, No Drawings

6-FLUORO-1,4-DIHYDRO-7-[4-(2-HYDROXYIMINOETHYL)-1-PIPERAZINYL]-4-OXOQUINOLINE-3-CARBOXYLIC ACID DERIVATIVES, THEIR PREPARATION AND PHARMACEUTICAL COMPOSITIONS

The following application is a divisional patent application of U.S. Ser. No. 09/489,058, , filed on Jan. 21, 2000, now abandoned, which claims priority from Taiwan patent application 089100389, filed on Jan. 12, 2000.

BACKGROUND OF THE INVENTION

1. Field of the Invention

The present invention relates to the method for preparing 6-fluoro-1,4-dihydro-7-[4-(2-hydroxyiminoethyl)-1-piperazinyl]-4-oxoquinoline-3-carboxylic acid derivatives, and the pharmaceutical composition comprising the derivatives as the active ingredient for the treatment of bacterial infections and/or renal cancer diseases.

2. Description of the Prior Art

It is known that a number of 6-fluoro-1,4-dihydroquinoline-3-carboxylic acid derivatives are highly potent broad-spectrum antibacteial agents [G. Y. Lesher et. al., *J. Med. Chem.*, 5, 259 (1962); D. Kaminsky et. al., *J. Med. Chem.*, 11, 160 (1968); J. Matsumoto et. al., *J. Med. Chem.*, 18, 74 (1975); H. Koga et. al., *J. Med. Chem.*, 23, 1358 (1980); J. Matsumoto et. al., *J. Med. Chem.*, 27, 292 (1984); I. Hayakawa et. al., *Chem. Pharm. Bull.*, 32, 4907 (1984); D. T. W. Chu et. al., *Drug. Fut.*, 10, 543 (1985); H. Kondo et. al., *J. Med. Chem.*, 29, 2020 (1986); D. T. W. Chu et. al., *J. Med. Chem.*, 29, 1531 (1986); K. Grohe et. al., *Liebigs Ann. Chem.*, 1, 29 (1987); J. M. Domagala et. al., *J. Med. Chem.*, 31, 991 (1988); H. Kondo et. al., *J. Med. Chem.*, 32, 671 (1989)]. These agents are shown to be specific inhibitors of the bacterial DNA gyrase, an enzyme which is responsible for negatively supercoiling covalently closed circular DNA and also in catenation and decatenation reactions. Compounds of this type, which have a piperazinyl radical in the 7-position, are described in the above publications, in U.S. Pat. Nos. 4,292,317, 4,528,287; R.O.C. Patent No. 047,572; and in the Japan Patent No. JP58069880, JP63083083 etc.

The inventors have found that the introduction into the above-mentioned compounds of a substituted iminoalkyl side chain [in particular 2-hydroxyimino-2-(4-methoxyphenyl)-ethyl] in the 4-position of piperazine, or a halogen atom (in particular a fluorine) in the 8-position, or both, gives new derivatives which possess potent antibacterial activity. These new derivatives are active at low concentrations against both Gram positive and Gram negative bacteria, including certain resistant strains, and thus are valuable agents for the treatment of infectious diseases. Due to their selective cytotoxicity, these compounds are also valuable agents for the treatment of renal cancer diseases. The present invention describes the preparation of 6-fluoro-1,4-dihydro-7-[4-(2-hydroxyiminoethyl)-1-piperazinyl]-4-oxoquinoline-3-carboxylic acid derivatives by an efficient means. The products described herein are suitable for large-scale production and exhibit very strong antibacterial activity. They have also exhibited strong activity against the growth of renal cancer cells.

SUMMARY OF THE INVENTION

In one aspect, the present invention features a method for preparing a compound of formula I comprising the steps of (a) reacting 1-ethyl-6-fluoro-1,4-dihydro-7-(1-piperazinyl)-4-oxoquinoline-3-carboxylic acid with a haloketon in a basic environment to form an intermidiate of formula II; and (b) treating said intermediate of formula with an amine to form said compound of formula I:

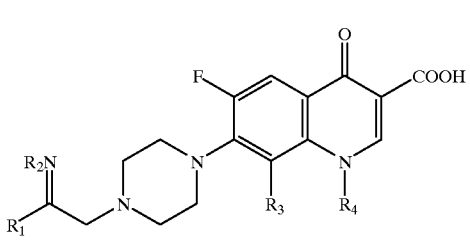

In another aspect, the present invention features a method for treating bacterial infections in a mammal, comprising administrating to the mammal an effective amount of a compound of fomula I.

In still another aspect, the present invention features a method for treating cancer diseases, especially renal cancer in a mammal, comprising administrating to the mammal an effective amount of a compound of fomula I.

In yet another aspect, the present invention features a pharmaceutical composition, which comprises an effective amount of a compound of formula I and a pharmaceutically aceptable carrier.

DETAILED DESCRIPTION OF THE INVENTION

According to one aspect of the present invention, new compounds of formula I can be prepared by the following reaction scheme:

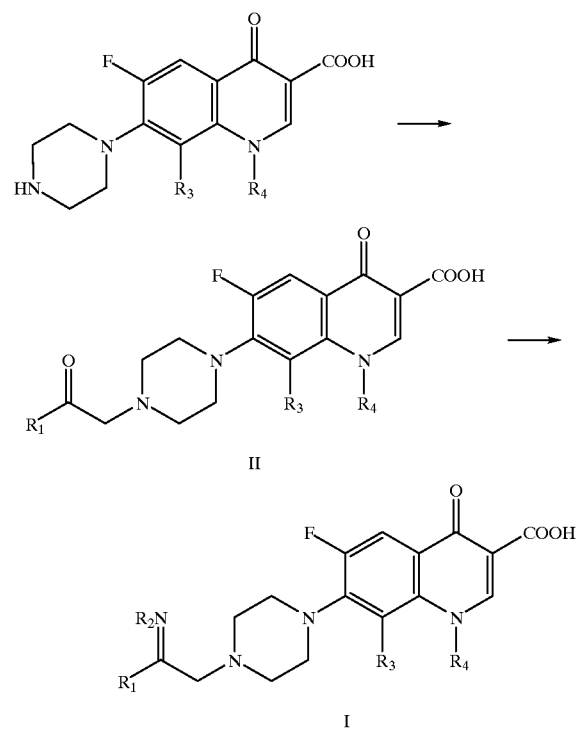

wherein:

$R_1$ is a $(C_1-C_4)$ alkyl or a phenyl group optionally substituted with one or two group selected from the group consisting of halide, $(C_1-C_4)$ alkyl, $(C_1-C_4)$ alkoxy, phenyl, nitro and amino;

$R_2$ represents hydroxyl, $(C_1-C_4)$ alkoxy, amino, $(C_1-C_4)$ alkyl or benzyl;

$R_3$ represents H or halide; and $R_4$ represents $(C_1-C_4)$ alkyl or a phenyl group optionally substituted with one or two group selected from the group consisting of halide, nitro and amino.

According to the method of the present invention, a compound of 1-ethyl-6-fluoro-1,4-dihydro-7-(1-piperazinyl)-4-oxoquinoline-3-carboxylic acid is first reacted with a haloketon in a basic environment to form an intermidiate of formula II. Then the intermidiate of formula II is treated with an amine to form the compound of formula I.

In this method, the basic environment may be created by adding basic compounds to the solution, the basic compounds including, but not limited to, $NaHCO_3$, $Na_2CO_3$, NaOH etc. The haloketons useful in the present invention include, but are not limited to, chloroacetone ($R_1=CH_3$), 2-bromoacetophenone ($R_1=C_6H_5$), 2-bromo-4'-fluoroacetophenone ($R_1=C_6H_4F$), 2-bromo-4'-chloroacetophenone ($R_1=C_6H_4Cl$), 2-bromo-4'-bromoacetophenone ($R_1=C_6H_4Br$), 2-bromo-4'-nitroacetophenone ($R_1=C_6H_4NO_2$), 2-bromo-4'-methoxyaceto-phenone ($R_1=C_6H_4OCH_3$). The haloketon described above may be dissolved in an organic solvent. Suitable organic solvents include, but are not limited to, for example N,N-dimethyl-formamide (DMF) or acetone. The reaction of the treatment with amine is well known by those skilled in the art.

According to the present invention, these active compounds, either as free type or their pharmaceutically acceptable salts, may be administered parentally or orally in a suitable pharmaceutical form. They also may be administered along or in conjunction with other antibacterial and/or anticancer agents, in combination with any pharmaceutically acceptable carrier.

As used herein, the pharmaceutically acceptable salts include salts with inorganic acids, such as hydrochloride, hydrobromide, sulfate and phosphate; salts with organic acids, such as acetate, maleate, tartrate, methanesulfonate; and salts with amino acids, such as arginine, aspartic acid and glutamic acid. Suitable pharmaceutical forms include sterile aqueous solutions or dispersions, sterile powders, tablets, troches, pills, capsules and the like. In addition, the active compounds may be incorporated into sustained-release preparations and formulations. The pharmaceutically acceptable carrier includes any and all solvents, disintegrating agents, binders, excipients, lubricants, absorption delaying agents and the like. Although the compound of the present invention may also be present as a hydrate or as a stereoisomer, it is a matter of course that these hydrates and stereoisomers are also included in the scope of the present invention.

Without intending to limit it in any manner, the present invention will be further illustrated by the following examples.

EXAMPLE 1

1-Ethyl-6-fluoro-7-[4-(2-hydrazinopropyl)-1-piperazinyl]-4-oxo-1,4-dihydroquinoline-3-carboxylic acid To a solution of the 1-ethyl-6-fluoro-1,4-dihydro-4-oxo-7-[4-(2-oxopropyl)-1-piperazinyl]-quinoline-3-carboxylic acid (0.38 g, 1 mmol) [H. Kondo et. al., *J. Med. Chem.*, 29, 2020 (1986)] in absolute methanol (20 ml) was added 85% hydrazine monohydrate (0.10 g, 2 mmol). The mixture was stirred for 18 hr at room temperature, then diluted with $CH_2Cl_2$ (50 ml). The organic phase was washed successively with water and brine, dried over $NaSO_4$, filtered and concentrated in vacuo to give a solid which was purified by flash column chromatography (silica gel, with $CH_2Cl_2$/methanol (10:1) as the eluent) and crystillization from $CH_2Cl$/methanol 5:1 to give 1-ethyl-6-fluoro-7-[4-(2-hydrazinopropyl)-1-piperazinyl]-4-oxo-1,4-dihydroquinone-3-carboxylic acid as an off-white amorphous solid (0.33 g, 83%). Mp: 208° C. (dec). $^1$H NMR (DMSO-$d_6$) δ1.41 (t, 3H, J=7.2), 1.71 (s, 3H), 2.63 (m, 4H), 2.97 (s, 2H), 3.28 (m, 4H), 4.58 (q, 2-H, J=7.2), 5.77 (s, 2H), 7.18 (d, 1H, J=7.6), 7.91 (d, 1H, J=13.2), 8.95 (s, 1H). Anal. Calcd. for $C_{19}H_{24}FN_5O_3$•$0.5H_2O$: C, 57.28; H, 6.32; N, 17.58. Found: C, 57.33; H, 6.23; N, 17.87.

EXAMPLE 2

1-Ethyl-6-fluoro-7-[4-(2-hydroxyiminopropyl)-1-piperazinyl]-4-oxo-1,4-dihydroquinoline-3-carboxylic acid To a suspension of the 1-ethyl-6-fluoro-1,4-dihydro-4-oxo-7-[4-(2-oxopropyl)-1-piperazinyl]-quinoline-3-carboxylic acid [H. Kondo et. al., *J. Med. Chem.*, 29, 2020 (1986)] (0.38 g, 1 mmol) in absolute methanol (20 ml) was added a solution of hydroxylamine hydrochloride (0.14 g, 2 mmol) and sodium bicarbonate (0.17 g, 2 mmol) in water (2 ml). The mixture was stirred for 20 hr at room temperature, then $CH_2Cl_2$ (50 ml) was added, and the layers were separated. The organic phase was washed successively with water and brine, dried over $Na_2SO_4$, filtered and concentrated in vacuo to give a solid which was purified by flash column chromatography (silica gel, with $CH_2Cl_2$/methanol (10:1) as the eluant) and crystillization from $CH_2Cl_2$/methanol 5:1 to give 1-ethyl-6-fluoro-7-[4-(2-hydroxyiminopropyl)-1-piperazinyl]-4-oxo-1,4-dihydroquinoline-3-carboxylic acid as an off-white amorphous solid (0.28 g, 72%). Mp: 218° C. (dec). $^1$H NMR (DMSO-$d_6$) δ1.41 (t, 3H, J=7.2), 1.81 (s, 3H), 2.54 (m, 4H), 3.03 (s, 2H), 3.33 (m, 4H), 4.57 (q, 2H, J=7.2), 7.17 (d, H, J=7.2), 7.90 (d, 1H, J=13.6), 8.92 (s, 1H), 10,61 (s, 1H), 15.27 (br s, 1H). Anal. Calcd. for $C_{19}H_{23}FN_4O_4$•$0.5H_2O$: C, 57.14; H. 6.06; N, 14.03. Found: C, 57.43; H, 5.87; N, 13.83.

EXAMPLE 3

1-Ethyl-6-fluoro-4-oxo-7-[4-(2-hydroxyimino-2-phenylethyl)-1-piperazinyl]-1,4-dihydroquinoline-3-carboxylic acid To a solution of the 1-ethyl-6-fluoro-1,4-dihydro-4-oxo-7-(4-phenacyl-1-piperazinyl)-quinoline-3-carboxylic acid (0.44 g, 1 mmole) [H. Kondo et. al., *J. Med. Chem.*, 29, 2020 (1986)] in absolute methanol (20 ml) was added a solution of hydroxylamine hydrochloride (0.14 g, 2 mmol) and sodium bicarbonate (0.17 g, 2 mmol) in water (2 ml). The mixture was heated at reflux for 36 hr and allowed to cool to room temperature. $CH_2Cl_2$ (50 ml) was added, and the layers were separated. The organic phase was washed successively with water and brine, dried over $Na_2SO_4$, filtered and concentrated in vacuo to give a solid which was purified by flash column chromatography (silica gel, with $CH_2Cl_2$/methanol (10:1) as the eluent) and crystillization from $CH_2Cl_2$/methanol (5:1) to give 1-ethyl-6-fluoro-4-oxo-7-[4-(2-hydroxyimino-2-phenylethyl)-1-piperazinyl]-1,4-dihydroquinoline-3-carboxylic acid as an off-white amorphous solid (0.31 g, 68%). Mp: 203° C. (dec). $^1$H NMR (DMSO-$d_6$) δ 1.38 (t, 3H, J=7.2), 2.64 and 3.25 (two m, 8H), 3.43 and 3.73 (two s, 2 H), 4.56 (q, 2H, J=7.2), 7.15 (d, 1H, J=7.2), 7.36–7.79 (m, 5H), 7.88 (d, 1H, J=13.2), 8.92 (s, 1H), 10.99 and 11.48 (two s, 1H), 15.07 (br s, 1H). Anal. Calcd. for $C_{24}H_{25}FN_4O_4 \cdot 1.5\ H_2O$: C, 60.10; H, 5.89; N, 11.68. Found: C, 60.19; H, 5.81; N, 11.64.

EXAMPLE 4

1-Ethyl-6,8-difluoro-1,4-dihydro-4-oxo-7-(4-phenacyl-1-piperazinyl)-quinoline-3-carboxylic acid A mixture of 1-ethyl-6,8-difluoro-4-oxo-7-(1-piperazinyl)-1,4-dihydroquinoline-3-carboxylic acid ( 0.5 1.48 mmole) [J. B. Cornett et. al., *Annu. Rep. Med. Chem.,* 21, 138 (1986).], sodium bicarbonate (0.12 g, 1.48 mmole), potassium iodide (0.08 g, 0.5 mmole), and 2-bromoacetophenone (0.37 g, 1.86 mmole) in DMF (40 ml) was stirred at room temperature for 3 hr, then poured into ice-water (50 ml), and extracted with $CH_2Cl_2$ (50 ml×3). The extract was washed with water, dried over $Na_2SO_4$, and evaporated. The residual solid was crystallized from ethanol-chloroform(5:1) to give 1-ethyl-6,8-difluoro-1,4-dihydro-4-oxo-7-(4-phenacyl-1-piperazinyl)-quinoline-3-carboxylic acid (0.49 g, 73%). Mp: 167° C. (dec). $^1$H NMR (DMSO-$d_6$) δ1.44 (t, 3H, J=7.0), 2.70 and 3.32 (two m, 8H), 3.97 (s, 2H), 4.59 (q, 2H, J=7.0), 7.54 and 8.02 (m, 5H), 7.85 (d, 1H, J=13.6), 8.92 (s, 1H), 14.95 (br s, 1H). Anal. Calcd. for $C_{24}H_{23}F_2N_3O_4 \cdot 0.5\ H_2O$: C, 62.06; H, 5.21; N, 9.05. Found: C, 62.18; H, 5.09; N, 9.06.

EXAMPLE 5

1-Ethyl-6-fluoro-7-{4-[2-hydroxyimino-2-(4-methoxyphenyl)-ethyl]-1-piperazinyl}-4-oxo-1,4-dihydroquinoline-3-carboxylic acid 1-Ethyl-6-fluoro-7-{4-[2-(4-methoxyphenyl)-2-oxoethyl]-1-piperazinyl}-4-oxo-1,4-dihydroquinoline-3-carboxylic acid was prepared from norfloxacin (0.50 g, 1.56 mmole) [H. Koga et. al., *J. Med. Chem.* , 23, 1358 (1980).] and 2-bromo-4'-methoxyacetophenone (0.43 g, 1.86 mmole) by a method similar to that described for Example 4 (75% yield). Mp: 202° C. (dec). $^1$H NMR (DMSO-$d_6$) δ 1.41 (t, 3H, J=7.0), 2.73 and 3.3 (two m, 8H), 3.85 (s, 3H), 3.88 (s, 2H), 4.58 (q, 2H, J=7.0), 7.02–7.2 (m, 3H), 7.87 (d, 1H, J=13.8), 8.01 (m, 2H), 8.94 (s, 1H), 15.33 (br s, 1H). Anal. Calcd. for $C_{25}H_{26}FN_3O_5$: C, 64.23; H, 5.61; N, 8.99. Found: C, 63.88; H, 5.61; N, 8.94.

1-Ethyl-6-fluoro-7-{4-[2-hydroxyimino-2-(4-methoxyphenyl)ethyl]-1-piperazinyl}-4-oxo-1,4-dihydroquinoline-3-carboxylic acid was prepared from 1-ethyl-6-fluoro-7-{4-[2-(4-methoxyphenyl)-2-oxoethyl]-1-piperazinyl}-4-oxo-1,4-dihydroquinoline-3-carboxylic acid (0.47 g, 1 mmole) and hydroxylamine hydrochloride (0.14 g, 2 mol) by a method similar to that described for Example 3 (74% yield). Mp: 221° C. (dec). $^1$H NMR (DMSO-$d_6$) δ 1.38 (t, 3H, J=7.2), 2.61 and 3.24 (two m, 8H), 3.41 and 3.77 (two s, 2H), 3.78 (s, 3H), 4.56 (q, 2H, J=7.2), 6.93 (m, 2H),7.15 (d, 1H, J=7.6),7.72 (m, 2H), 7.89 (d, 1H, J=13.6), 8.93 (s, 1H), 10.95 and 11.26 (two s, 1H), 15.29 (br s, 1H). Anal. Calcd. for $C_{25}H_{27}FN_4O_5 \cdot 0.25\ H_2O$: C, 61.66; H, 5.69; N, 11.50. Found: C, 61.61; H, 5.70; N, 11.27.

EXAMPLE 6

1-Ethyl-6,8-difluoro-7-{4-[2-hydroxyimino-2-(4-methoxyphenyl)ethyl]-1-piperazinyl}-4-oxo-1,4-dihydroquinoline-3-carboxylic acid 1-Ethyl-6,8-difluoro-7-{4-[2-(4-methoxyphenyl)-2-oxoethyl]-1-piperazinyl}-4-oxo-1,4-dihydroquinoline-3-carboxylic acid was prepared from 1-ethyl-6,8-difluoro-4-oxo-7-(1-piperazinyl)-1,4-dihydroquinoline-3-carboxylic acid (0.50 g, 1.48 mmole) and 2-bromo-4'-methoxyacetophenone (0.43 g, 1.86 mmole) by a method similar to that described for Example 4 (63% yield). Mp: 190° C. (dec). $^1$H NMR (DMSO-$d_6$) δ 1.44 (t, 3H, J=7.0), 2.69 and 3.24 (two m, 8H), 3.84 (s, 3H), 3.87 (s, 2H), 4.58 (q, 2H, J=7.0), 7.05 (m, 2H), 7.85 (d, 1H), J=12.0), 8.01 (m, 2H), 8.92 (s, 1H), 14.92 (br s, 1H). Anal. Calcd. for $C_{25}H_{25}F_2N_3O_5 \cdot 0.25\ H_2O$: C, 61.28; H, 5.25; N, 8.58. Found: C, 61.25; H, 5.23; N, 8.67.

1-Ethyl-6,8-difluoro-7-{4-[2-hydroxyimino-2-(4-methoxy-phenyl)ethyl]-1-piperazinyl}-4-ozo-1,4-dihydroquinoline-3-carboxylic acid was prepared from 1-ethyl-6,8-difluoro-7-{4-[2-(4-methoxyphenyl)-2-oxoethyl]-1-piperazinyl}-4-oxo-1,4-dihydroquinoline-3-carboxylic acid (0.49 g, 1 mmole) and hydroxylamine hydrochloride (0.14 g, 2 mmol) by a method similar to that described for Example 3 (63% yield). Mp: 176° C. (dec). $^1$H NMR (DMSO-$d_6$) δ 1.42 (t, 3H, J=7.0), 2.58 and 3.29 (two m, 8H), 3.40 and 3.69 (two s, 2H), 3.78 (s, 3H), 4.57 (q, 2H, J=7.0), 6.94 and 7.73 (two m, 4H), 7.83 (d, 1H, J=12.0), 8.91 (s, 1H), 10.94 and 11.25 (two s, 1H), 14.90 (br s, 1H) . Anal. Calcd. for $C_{25}H_{26}F_2N_4O_5 \cdot 0.5\ H_2O$: C, 58.93; H, 5.34; N, 11.00. Found: C, 59.02; H, 5.21; N, 10.92.

EXAMPLE 7

1-Ethyl-6-fluoro-7-{4-[2-methoxyimino-2-(4-methoxyphenyl)-ethyl]-1-piperazinyl}-4-oxo-1,4-dihydroquinoline-3-carboxylic acid 1-Ethyl-6-fluoro-7-{4-[2-methoxyimino-2-(4-methoxyphenyl)ethyl]-1-piperazinyl}-4-oxo-1,4-dihydroquinoline-3-carboxylic acid was prepared from 1-ethyl-6-fluoro-7-{4-[2-(4-methoxyphenyl)-2-oxoethyl]-1-piperazinyl}-4-oxo-1,4-dihydroquinoline-3-carboxylic acid (0.23 g, 0.5 mmol) and O-methylhydroxylamine hydrochloride (0.08 g, 1 mmol) by a method similar to that described for Example 3 (68% yield). Mp: 165° C. (dec). $^1$H NMR (DMSO-$d_6$) δ 1.38 (t, 3H, J=7.0), 2.61 and 3.23 (two m, 8H), 3.69 and 3.79 (m, 6H), 3.89 (s, 2H), 4.54 (q, 2H, J=7.0), 6.93 (m, 2H), 7.13 (d, 1H, J=7.2), 7.73 (m, 2H), 7.89 (d, 1H, J=13.2), 8.90 (s, 1,H) 15.35 (br s, 1H). Anal. Calcd. for $C_{26}H_{29}FN_4O_5H_2O$: C, 60.69; H, 6.07; N, 10.88. Found: C, 60.90; H, 5.77; N, 10.62.

EXAMPLE 8

1-(4-Nitro-2-fluorophenyl)-6-fluoro-7-{4-[2-hydroxyimino-2-(4-methoxyphenyl)ethyl]-1-piperazinyl}-4-oxo-1,4-dihydroquinoline-3-carboxylic acid To a solution of the 1-(4-nitro-2-fluorophenyl)-6-fluoro-7-(1-piperazinyl)-4-oxo-1,4-dihydro-quinoline-3-carboxylic acid (0.43 g, 1 mmol) in DMF (15 ml) was added 2-bromo-4'-methoxyacetophenone (0.29 g, 1.28 mmol) and sodium bicarbonate (0.08 g, 1 mmol). The reaction mixture was stirred for 24 hr at room temperature. After removing the solvent, the residue was taken up by $CH_2Cl_2$, solution, and after washed with water and dried with $Na_2SO_4$, was evaporated to dryness. Crystallization of the solid residue from $CH_2Cl_2$/methanol (10:1) afforded the desired 1-(4-nitro-2-fluorophenyl)-6-fluoro-7-{4-[2-(4-methoxyphenyl)-2-oxoethyl]-1-piperazinyl}-4-oxo-1,4-dihydroquinoline-3-carboxylic acid (0.37 g, 86%). Mp: 136° C. (dec). $^1$H NMR (DMSO-$d_6$) δ 2.63 and 3.10 (two m, 8),3.81–3.83 (m, 5H) 6.40 (d, 1H, J=6.8), 7.01 (d, 2H, J=9.0), 7.94–8.03 (m, 3H), 8.17–8.56 (m, 3H), 8.93 (s, 1H), 14.88 (br s, 1H). Anal. Calcd. for $C_{29}H_{24F2}N_4O_7 \cdot H_2O$: C, 58.39; H, 4.39; N, 9.39. Found: C, 58.75; H, 4.42; N, 9.20.

To a solution of the 1-(4-nitro-2-fluorophenyl)-6-fluoro-7-{4-[2-(4-methoxyphenyl)-2-oxoethyl]piperazinyl}-4- oxo-1,4-dihydroquinoline-3-carboxylic acid (0.58 g, 1 mmol) in absolute ethanol (20 ml) were added hydroxylamine hydrochloride (0.14 g, 2 mmol) and sodium bicarbonate (0.17 g, 2 mmol) dissolved in distilled water (2 ml). The reaction mixture was refluxed for 20 hr, then diluted with $CH_2Cl_2$ (50 ml). The organic phase was washed successively with water and brine, dried over anhydrous $Na_2SO_4$, filtered and concentrated in vacuo to give a pale yellow solid which was purified by flash column chromatography (silica gel, with $CH_2Cl_2$/methanol (10:1) as the eluant) and crystillization from $CH_2Cl_2$/methanol 5:1 to give 1-(4-nitro-2-fluorophenyl)-6-fluoro-7-{4-[2-hydroxyimino-2-(4-methoxy-phenyl)ethyl]-1-piperazinyl}-4-oxo-1,4-dihydroquinoline-3-carboxylic acid (0.46 g, 80% yield). Mp: 216° C. (dec). $^1H$ NMR (DMSO-$d_6$) δ 2.54 and 3.02 (two n, 8H), 3.63 (s, 2H), 3.76 (s, 3H), 6.36 (d, 1H, J=6.8), 6.89 (d, 2H, J=8.8), 7.67 (d, 2H, J=8.8), 7.98 (d, 1H, J=13.2), 8.12–8.53 (m, 3H) 8.91 (s, 1H), 11.22 (s, 1H), 14.85 (br s, 1H) . Anal. Calcd. for $C_{29}H_5F_2N_5O_7$•2.5 $H_2O$: C, 54.55; H, 4.74; N, 10.97. Found: C, 54.19; H, 4.36; N, 10.66.

EXAMPLE 9

1-Ethyl-6-fluoro-7-{4-[2-(4-fluorophenyl)-2-hydroxyimino-ethyl]-1-piperazinyl}-4-oxo-1,4-dihydro-3-quinolinecarboxylic acid 1-Ethyl-6-fluoro-7-{4-[2-(4-fluorophenyl)-2-oxoethyl]-1-piperazinyl}-4-oxo-1,4-dihydro-3-quinolinecarboxylic acid was prepared from norfloxacin (0.5 g, 1.56 mmole) and 2-bromo-4'-fluoroaceto-phenone(0.40 g, 1.86 mmole) by a method similar to that described for Example 4 (61% yield). Mp: 208° C. (dec). $^1H$ NMR (DMSO-$d_6$) δ 1.41 (t, 3H, J=7.0), 2.73 and 3.3 (two m, 8H), 3.94 (s, 2H), 4.58 (q, 2 H. J=7.0), 7.18 (d, 1H, J=7.0), 7.36 (m, 2H), 7.90 (d, 1H, J=13.2), 8.11 (m, 2H), 8.94 (s, 1H), 15.30 (br s, 1H). Anal. Calcd. for $C_{24}H_{23}F_2N_3O_4$: C, 63.29; H, 5.09; N, 9.23. Found: C, 62.96; H, 5.19; N, 9.16.

1-Ethyl-6-fluoro-7-{4-[2-(4-fluorophenyl)-hydroxyiminoethyl]-1-piperazinyl}-4-oxo-1,4-dihydro-3-quinolinecarboxylic acid was prepared from 1-ethyl-6-fluoro-7-{4-[2-(4-fluorophenyl)-2-oxoethyl]-1-piperazinyl}-4-oxo-1,4-dihydro-3-quinolinecarboxylic acid (0.23 g, 0.5 mmole) and hydroxylamine hydrochloride (0.07 g, 1 mmol) by a method similar to that described for Example 3 (66% yield). $^1H$ NMR (DMSO-$d_6$): δ 1.39 (t, 3H, J=7.2), 2.62 and 3.25 (two m, 8H), 3.44 and 3.73 (two s, 2H), 4.57 (q, 2H, J=7.2), 7.15 (d, 1H, J=7.2), 7.42–7.83 (m, 4H),7.89 (d, 1H, J=13.3), 8.93 (s, 1H), 11.19 and 11.62 (two s, 1H), 15.23 (br s, 1H) Anal. Calcd. for $C_{24}H_{24}F_2N_4O_4$•0.5 $H_2O$: C, 60.12; H, 5.26; N, 11.68. Found: C, 60.01; H, 5.24; N, 11.60.

EXAMPLE 10

1-Ethyl-6-fluoro-7-{4-[2-(4-chlorophenyl)-2-hydroxyimino-ethyl]-1-piperazinyl}-4-oxo-1,4-dihydro-3-quinolinecarboxylic acid 1-Ethyl-6-fluoro-7-{4-[2-(4-chlorophenyl)-2-oxoethyl]-1-piperazinyl}-4-oxo-1,4-dihydro-3-quinolinecarboxylic acid was prepared from norfloxacin (0.5 g, 1.56 mmole) and 2-bromo-4'-chloroaceto-phenone(0.43 g, 1.86 mmole) by a method similar to that described for Example 4 (67% yield). Mp: 207° C. (dec). $^1H$ NMR (DMSO-$d_6$) δ 1.41 (7, 3H, J=7.2), 2.73 and 3.29 (two m, 8H), 3.95 (s, 2H), 4.58 (q, 2H, J=7.2 7.19 (d, 1H, J=7.2), 7.59 and 8.02 (m, 4H), 7.92 (d, 1H, J=13.2), 8.95 (s, 1H), 15.41 (br s, 1H). Anal. Calcd. for $C_{24}H_{23}ClFN_3O_4$•0.25$H_2O$: C, 60.51; H, 4.97; N, 8.82. Found: C, 60.49; H, 4.96; N, 8.82.

1-Ethyl-6-fluoro-7-{4-[2-(4-chlorophenyl)-2-hydroxyiminoethyl]-1-piperazinyl}-4-oxo-1,4-dihydro-3-quinoline-carboxylic acid was prepared from 1-ethyl-6-fluoro-7-{4-[2-(4-chlorophenyl)-2-oxoethyl]-1-piperazinyl}-4-oxo-1,4-dihydro-3-quinolinecarboxylic acid (0.24 g, 0.5 mmole) and hydroxylamine hydrochloride (0.07 g, 1 mmol) by a method similar to that described for Example 3 (73% yield). $^1H$ NMR (DMSO-$d_6$) δ 1.39 (t, 3H, J=7.0), 2.61 and 3.24 (two m, 8H), 3.44 and 3.73 (two s, 2H), 4.56 (q, 2H, J=7.0), 7.24 and 7.78 (two m, 5H), 7.89 (d, 1H, J=13.4), 8.93 (s, 1H), 11.03 and 11.49 (two s, 1 H), 15.35 (br s, 1H). Anal. Calcd. for $C_{24}H_{24}FClN_4O_4$•0.25 $H_2O$: C, 58.66; H, 5.02; N, 11.40. Found: C, 58.48; H, 5.01; N, 11.29.

EXAMPLE 11

1-Ethyl-6,8-difluoro-7-{4-[2-(4-fluorophenyl)-2-hydroxyiminoethyl]-1-piperazinyl}-4-oxo-1,4-dihydro-3-quinolinecarboxylic acid 1-Ethyl-6,8-difluoro-7-{4-[2-(4-fluorophenyl)-2-oxoethyl]-1-piperazinyl}-4-oxo-1,4-dihydro-3-quinolinecarboxylic acid was prepared from 1-ethyl-6,8-difluoro-4-oxo-7-(1-piperazinyl)-1,4-dihydro-quinoline-3-carboxylic acid (0.50 g, 1.48 mmole) and 2-bromo-4'-fluoroacetophenone (0.40 g, 1.86 mmole) by a method similar to that described for Example 4 (64% yield). Mp: 170° C. (dec). $^1H$ NMR (DMSO-$d_6$) δ 1.44 (t, 3H, J=7.0), 2.70 and 3.3 (two m, 8H), 3.94 (s, 2H), 4.58 (q, 2H, J=7.0), 7.37 (n, 2H), 7.90 (d, 1H, J=11.8), 8.11 (m, 2H), 8.92 (s, 1H), 14.92 (br s, 1H). Anal. Calcd. for $C_{24}H_{22}F_3N_3O_4$•0.5 $H_2O$: C, 59.75; H, 4.80; N, 8.71. Found: C, 59.39; H, 4.66; N, 8.62.

1-Ethyl-6,8-difluoro-7-{4-[2-(4-fluorophenyl)-2-hydroxyiminoethyl]-1-piperazinyl}-4-oxo-1,4-dihydro-3-quinolinecarboxylic acid was prepared from 1-ethyl-6,8-difluoro-7-{4-[2-(4-fluorophenyl)-2-oxoethyl]-1-piperazinyl}-4-oxo-1,4-dihydro-3-quinolinecarboxylic acid (0.24 g, 0.5 mmole) and hydroxylamine hydrochloride (0.07 g, 1 mmol) by a method similar to that described for Example 3 (70% yield). Mp: 201° C. (dec). $^1H$ NMR (DMSO-$d_6$) δ 1.42 (t, 3H, J=7.0), 2.58 and 3.29 (two m, 8H), 3.41 and 3.73 (two s, 2H), 4.57 (q, 2H, J=7.0), 7.44–7.87 (m, 4 H), 7.90 (d, 1H, J=12.0), 8.95 (s, 1H), 11.18 and 11.65 (two s, 1H), 14.92 (br s, 1H). Anal. Calcd. for $C_{24}H_{23}F_3N_4O_4$•0.5 $H_2O$: C, 57.95; H, 4.86; N, 11.26. Found: C, 57.91; H, 4.83; N, 11.12.

EXAMPLE 12

1-(4-amino-2-fluorophenyl)-6-fluoro-7-{4-[2-(4-methoxyphenyl)-2-oxoethyl]-1-piperazinyl}-4-oxo-1,4-dihydroquinoline-3-carboxylic acid To a suspension of the 1-(2-fluoro-4-nitrophenyl)-6-fluoro-7-{4-[2-(4-methoxyphenyl)-2-oxoethyl]-1-piperazinyl}-4-oxo-1,4-dihydroquinoline-3-carboxylic acid [example 8] (0.58 g, 1 mmol) in ethanol (20 ml) was hydrogenated overnight in hydrogen in the presence of 10% Pd/C (25 mg) at room temperature. The reaction mixture was filtered and the filtrate was evaporated in vacuo to give a solid, the resulting solid was recrystallized from ethanol to afford 1-(4-amino-2-fluorophenyl)-6-fluoro-7-{4-[2-(4-methoxyphenyl)-2-oxoethyl]-1-piperazinyl}-4-oxo-1,4-dihydroquinoline-3-carboxylic acid (0.28 g, 51%). Mp: 143° C. (dec). $^1H$ NMR (DMSO-$d_6$) δ 2.66 and 3.09 (two m, 8H), 3.85-3.84 (m, 5H), 6.05 (s, 2H), 6.47 (d, 1H, J=7.2), 6.58 (m, 2H), 7.02 (m, 2H), 7.36 (m, 1H), 7.97 (m, 3H), 8.62 (s, 1H), 15.06 (br s, 1H). Anal. Calcd. for $C_{29}H_{26}F_2N_4O_5$•1.0 $H_2O$: C, 61.48; H, 4.98; N, 9.89. Found: C, 61.81; H, 4.85; N, 9.81.

EXAMPLE 13

Antibacterial Activity

In the determination of minimal inhibition concentration (MIC), 2 mg of each test compound was dissolved in an appropriate solvent (100% DMSO) and serially diluted into the desired testing concentration ranges. Each series of testing solution (0.01 ml) was added into the 48-well plate with 0.99 ml of media broth containing $1-5\times10^5$ CFU/ml testing microorganism. Thus the final maximal concentration of DMSO was 1% and the initial concentration of testing solution was 300 μM. Media used were as follows: Nutrient Broth (NB, DIFCO) for *Escherichia coli*, *Pseudomonas aeruginosa* and *Klebsiella pneumoniae;* Mueller-Hinton broth (DIFCO) for *Staphylococcus aureus*, Methicillin Resistant (MRSA) and *Proteus vulgaris;* Brain Heart Infusion broth (BHI, DIFCO) for *Mycobacterium ranae.* Tryptic Soy Broth (DIFCO) containing of 7% calf serum for *Streptococcus pneumoniae* (EM & AM Res. Clinical Isolates) and *Enterococcus faecalis* (VRE, Clinical Isolates). The plates were incubated for 20–72 hours at 37° C., then the MIC was determined by visual turbidity readout or by microscope observation of microorganism growth. Vehicle and reference agents were used in every test as the negative and positive controls, and the assays were performed in duplicate. The results are shown in Table 1 as follows:

257); ovarian cancer (IGROV1, OVCAR-3, OVCAR-4, OVCAR-5, OVCAR-8, and SK-OV-3); renal cancer (786-0, A498, ACHN, CAKI-1, RXF 393, 2C, TK-10, and UO-31); prostate cancer (PC-3 and DU-145); and breast cancer (MCF7, MCF7/ADR-RES, MDA-MB-231/ATCC, HS 578T, MDA-MB-435, MDA-N, and T-47D). For each compound, dose-response curves for each cell line were measured with five different drug concentrations, and the concentration causing 50% cell growth inhibition ($GI_{50}$) compared with the control was calculated. Table 2 summarizes the representative $GI_{50}$ values, the mean $GI_{50}$ values for all the 60 tumor cell lines, and the range to indicate the ratio of $GI_{50}$ for the least sensitive and the most sensitive cells of three tested compounds (Exp. 5, Exp. 9, and Exp. 10). All of them proved to be active against the growth of renal (CAKI-1, RXF-393, UO-31) cancer cell lines with a $GI_{50}$ ranged from 0.03 to 6.91 μM. The data reveal an excellent selectivity of the compounds of the present invention for the renal cancer cells.

TABLE 1

In vitro antibacterial activity of 4-oxoquinoline-3-carboxylic acid derivatives (MIC, μM)

|  | MRSA | Ec | Mr | Pa | Kp | Pv | SpEAR | EfVRE |
|---|---|---|---|---|---|---|---|---|
| Exp. 1 | 4.01 | 2.01 | 16.1 | 16.1 | 0.064 | 2.01 | 32.1 | 16.1 |
| Exp. 2 | 0.51 | 0.51 | 32.1 | 16.0 | 0.13 | 2.00 | nd[a] | nd |
| Exp. 3 | 0.44 | 0.86 | 55.3 | 13.8 | 0.22 | 3.45 | nd | nd |
| Exp. 4 | 1.71 | 0.22 | 3.43 | 0.86 | 0.055 | 0.22 | 13.7 | 13.7 |
| Exp. 5 | 0.41 | 1.62 | 104 | 25.9 | 0.027 | 3.24 | 12.97 | 3.24 |
| Exp. 6 | 0.20 | 0.40 | 6.34 | 3.16 | 0.10 | 0.40 | 6.34 | 3.16 |
| Exp. 7 | 1.57 | 6.31 | 202 | 202 | 1.57 | 6.31 | 12.6 | 12.6 |
| Exp. 8 | 0.34 | 1.32 | 21.1 | 42.2 | 0.08 | >169 | 1.32 | 5.28 |
| Exp. 11 | 0.61 | 0.61 | >200 | 6.14 | 0.06 | 0.61 | 6.14 | 2.05 |
| Exp. 12 | 0.55 | 0.55 | 18.2 | 5.74 | 0.05 | 18.2 | 1.82 | 5.47 |
| Gentamicin[b] | 0.78 | 0.20 | 0.20 | 0.39 | 0.2 | 0.1 | 100 | 50 |
| Norfloxacin | 4.89 | 0.63 | 9.81 | 1.22 | 0.041 | 0.16 | 19.6 | 9.81 |
| Ofloxacin | 1.08 | 0.28 | 1.08 | 2.16 | 0.036 | 0.069 | 4.32 | 4.32 |

Abbreviation: MRSA: *Staphylococcus aureus*, Methicillin Resistant; Ec: *Escherichia coli;* EfVRE Mr: *Mycobacterium ranae;* Pa: *Pseudomonas aeruginosa;* Kp: *Klebsiella pneumoniae;* Pv: *Proteus vulgaris;* SpEAR: *Staphylococcus pneumoniae,* Erythromycin and Ampicillin resistant, clinical isolates; EfVRE: *Enterococcus faecalis,* Vancomycin resistant, clinical isolates.
[a]Not determined.
[b]MIC, in μg/ml.

EXAMPLE 14

Anticancer Activity

All these compounds were evaluated in vitro against 60 human tumor cell lines derived from nine cancer cell types: leukemia (CCRF-CEM, HL-60 (TB), K-562, MOLT-4, RPMI-8226, and SR); non-small cell lung cancer (A549/ATCC, EKVX, HOP-62, HOP-92, NCI-H226, NCI-H23, NCI-H322M, and NCI-H522); colon cancer (COLO 205, HCC-2998, HCT-116, HCT-15, HT29, KM12, and SW-620); CNS cancer (SF-268, SF-295, SF-539, SNB-19, SNB-75, and U251); melanoma (LOX IMVI, MALME-3M, M14, SK-MEL-2, SK-MEL-28, SK-MEL-5, and UACC-

TABLE 2

Inhibition of in vitro cancer cell lines by 4-oxoquinoline-3-carboxylic acid derivatives [$GI_{50}$ (μM)][a]

| Cell Line | Exp. 9 | Exp. 10 | Exp. 5 |
|---|---|---|---|
| Leukemia |  |  |  |
| CCRF-CEM | 10.5 | 67.4 | 24.4 |
| HL-60 (TB) | 0.98 | 1.29 | 17.7 |
| RPMI-8226 | 22.9 | 3.21 | 38.4 |
| Non-Small Cell Lung Cancer |  |  |  |
| EKVX | 42.6 | 19.2 | 46.8 |
| HOP-62 | 42.6 | 28.6 | 52.3 |
| NCI-H226 | 53.5 | 20.3 | 93.3 |
| Ovarian Cancer |  |  |  |
| SK-OV-3 | 32.0 | 28.7 | 37.2 |
| SK-OV-4 | 39.4 | 32.1 | 55.1 |

TABLE 2-continued

Inhibition of in vitro cancer cell lines by 4-oxoquinoline-3-carboxylic acid derivatives [GI$_{50}$ (μM)][a]

| Cell Line | Exp. 9 | Exp. 10 | Exp. 5 |
|---|---|---|---|
| SK-OV-5 | >100 | 22.8 | >100 |
| Renal Cancer | | | |
| CAKI-1 | 1.89 | 0.40 | 6.91 |
| RXF-393 | 0.17 | 0.72 | nd[b] |
| UO-31 | 0.13 | 0.03 | 0.55 |
| Mean[c] | 21.5 | 9.31 | 31.8 |
| Range[d] | 758 | 2291 | 182 |

[a]Data obtained from NCI's in vitro disease-oriented tumor cells screen. GI$_{50}$: Drug molar concentration causing 50% cell growth inhibition.
[b]Not determined.
[c]Mean values over 60 cell lines tested.
[d]Ratio of GI$_{50}$ value for the least sensitive cell to the most sensitive cell.

While the invention has been particularly shown and described with the reference to the preferred embodiment thereof, it will be understood by those skilled in the art that various changes in form and details may be made without departing from the spirit and scope of the invention.

What is claimed is:

1. A method for treating renal cancer in a mammal, comprising administering to said mammal an effective amount of a compound of fomula I:

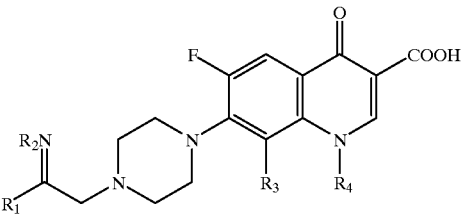

I or the stereoisomers or hydrates thereof, or their pharmaceutically aceptable salts, wherein:

$R_1$ is ($C_1$–$C_4$) alkyl or phenyl optionally substituted with one or two group selected from the group consisting of halide, ($C_1$–$C_4$) alkyl, ($C_1$–$C_4$) alkoxy, phenyl, nitro and amino;

$R_2$ represents hydroxyl, ($C_1$–$C_4$) alkoxy, amino, ($C_1$–$C_4$) alkyl or benzyl;

$R_3$ represents H or halide; and $R_4$ represents ($C_1$–$C_4$) alkyl or phenyl optionally substituted with one or two group selected from the group consisting of halide, nitro and amino.

* * * * *